United States Patent [19]
Capetan et al.

[11] Patent Number: 5,718,677
[45] Date of Patent: Feb. 17, 1998

[54] SOFT ASPRIATION TIP

[75] Inventors: Thomas G. Capetan, Corona Del Mar; Valentine P. Injev, Irvine, both of Calif.

[73] Assignee: Alcon Laboratories, Inc., Fort Worth, Tex.

[21] Appl. No.: 800,370

[22] Filed: Feb. 14, 1997

[51] Int. Cl.⁶ .................................................. A61M 1/00
[52] U.S. Cl. ........................ 604/35; 604/239; 606/107
[58] Field of Search ........................ 604/35, 22, 239, 604/27, 118, 119, 280; 606/107, 171, 169

[56] References Cited

U.S. PATENT DOCUMENTS

| | | | |
|---|---|---|---|
| 4,487,600 | 12/1984 | Brownlie et al. | 604/35 |
| 4,710,180 | 12/1987 | Johnson | 604/239 |
| 5,084,012 | 1/1992 | Kelman . | |
| 5,133,159 | 7/1992 | Nelson . | |
| 5,217,465 | 6/1993 | Steppe . | |
| 5,242,449 | 9/1993 | Zaleski | 604/35 X |
| 5,290,892 | 3/1994 | Namdaran et al. . | |
| 5,364,405 | 11/1994 | Zaleski . | |
| 5,403,901 | 4/1995 | Namdaran et al. . | |
| 5,433,746 | 7/1995 | Namdaran et al. . | |
| 5,514,086 | 5/1996 | Parisi et al. | 604/22 |

OTHER PUBLICATIONS

Edward Weck & Company, Inc.; *Week Eye Instruments;* 1975.
Coopervision Surgical; *Coopervision Surgical Systems and Supplies;* 1986; pp. 2.6, 2.7.

*Primary Examiner*—John D. Yasko
*Attorney, Agent, or Firm*—Jeffrey S. Schira

[57] ABSTRACT

An aspiration tip having a relatively rigid cannula attached to a hub and an open end opposite the hub. The open end is sealed with a cap made from a soft, flexible material, such as rubber or soft plastic. The soft material reduces the likelihood that the posterior capsule will tear during cortical clean-up and capsule polishing.

6 Claims, 1 Drawing Sheet

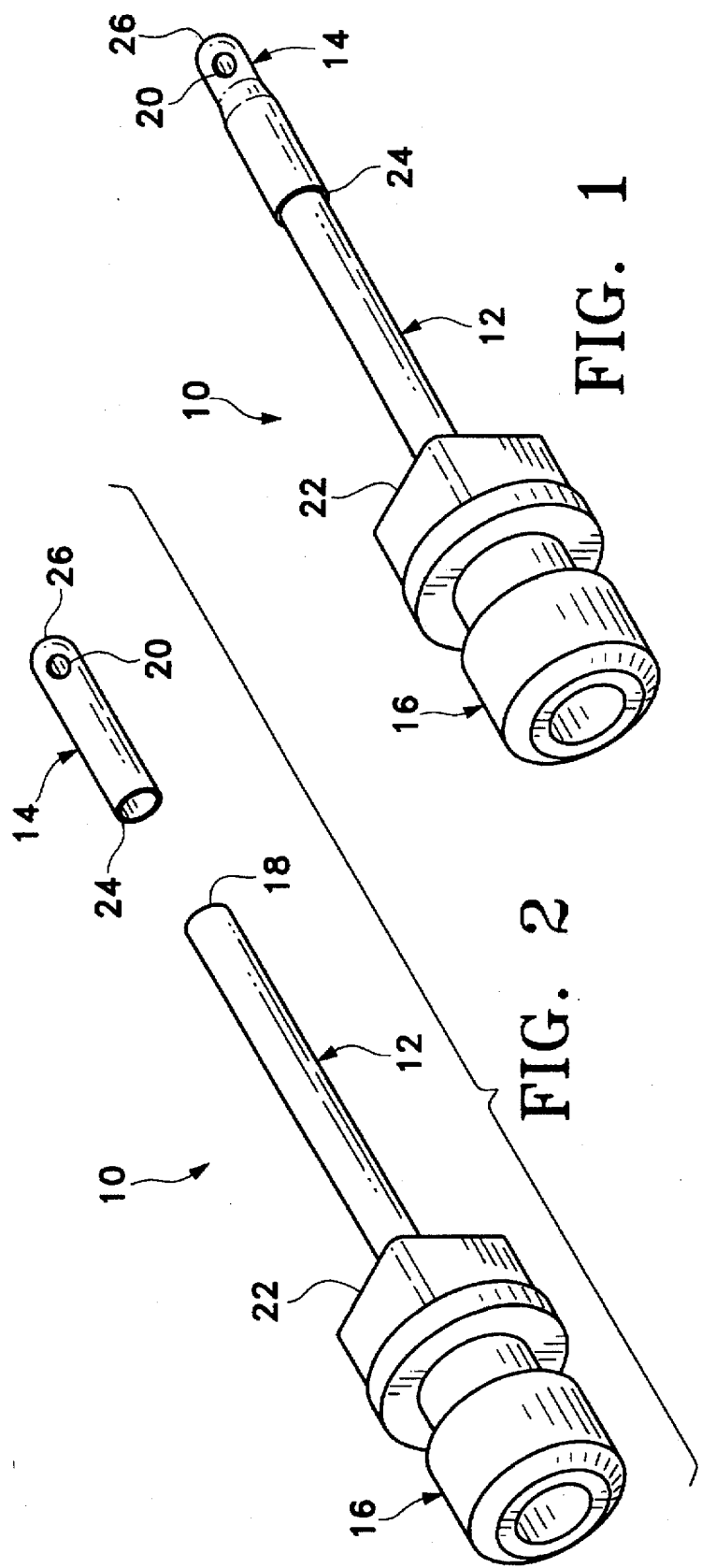
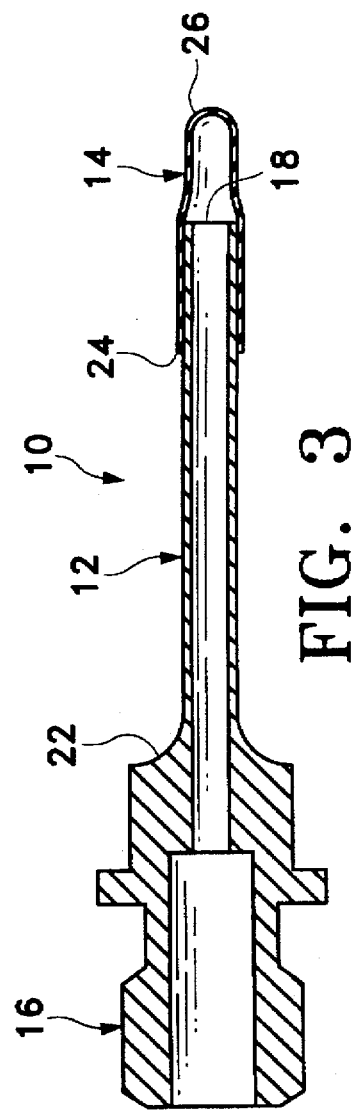

SOFT ASPIRATION TIP

This invention relates to aspiration tips and more particularly to aspiration tips used in ophthalmic phacoemulsification surgery.

BACKGROUND OF THE INVENTION

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial lens.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by the artificial lens.

Prior to the introduction of the artificial intraocular lens into the eye, softer cortical material is aspirated from the eye using an aspiration tip. Aspiration tips are similar to phacoemulsification tips, but smaller and not typically vibrated ultrasonically. The aspiration tip may also be used to "polish" the posterior capsule to remove residual epithelial cells and reduce the risk of posterior capsule opacification. Conventional aspiration tips are made from titanium or stainless steel. These tip must be highly polished to reduce burrs which may snag or tear the posterior capsule. Polishing the aspiration port and the interior lumen of the aspiration tip, however, is very difficult and some burrs may remain even after extensive polishing. During capsule polishing and cortical clean-up, the posterior capsule may be drawn partially into the aspiration port and interior lumen of the aspiration tip. If these portions of the aspiration tip contains rough edges or burrs, tearing of the posterior capsule can occur. In addition, during repeated use, the exterior of the aspiration tip can develop burrs and rough spots that can snag or tear the capsule.

Accordingly, a need continues to exists for an aspiration tip that reduces the possibility of tearing the posterior capsule during cortical clean-up and capsule polishing.

BRIEF SUMMARY OF THE INVENTION

The present invention improves upon prior art aspiration tips by providing an aspiration tip having a relatively rigid cannula attached to a hub and an open end opposite the hub. The open end is sealed with a cap made from a soft, flexible material, such as rubber or soft plastic. The soft material reduces the likelihood that the posterior capsule will tear during cortical clean-up and capsule polishing.

One objective of the present invention is to provide an aspiration tip that reduces the likelihood of tearing the posterior capsule.

Another objective of the present invention is to provide an aspiration tip having an open lumen sealed with a flexible cap.

Other objectives, features and advantages of the present invention will become apparent with reference to the drawings, and the following description of the drawings and claims.

BRIEF DESCRIPTION OF THE DRAWINGS

FIG. 1 is a perspective view of one embodiment of the present invention.

FIG. 2 is an expanded perspective view of the embodiment of the invention illustrated in FIG. 1 showing the cap removed from the lumen.

FIG. 3 is a cross-sectional view of the embodiment illustrated in FIG. 1 taken along the longitudinal axis of the cannula.

DETAILED DESCRIPTION OF THE INVENTION

Aspiration tip 10 of the present invention generally consists of cannula 12 and cap 14. Cannula 12 is open at distal end 18 and is attached to hub 16 at proximal end 22. Hub 16 allows aspiration tip 10 to be attached to an appropriate handpiece (not shown) in a manner well-known in the art. Cannula 12 and hub 16 preferably are made from titanium or stainless steel, but other relatively rigid metals or plastic may also be used. Cannula preferable is between 0.01 inches and 0.04 inches in diameter, and between 0.50 inches and 1.00 inches long.

Distal end 18 is sealed by cap 14. Cap 14 is generally tubular in shape, is open on proximal end 24 and closed on distal end 26 except for port 20. Cap 14 may be relatively straight or may be formed at any angle or curve suitable for aspirating the interior regions of the eye. Port 20 is of suitable size, shape and location well-known to those in the art. Cap 14 preferably is between approximately 0.01 inches and 0.75 inches long and elastic enough to be stretched over cannula 12, as seen in FIGS. 2 and 3. Cap 14 preferably is molded from a relatively soft rubber or plastic, such as silicone rubber or the acrylic materials disclosed in U.S. Pat. Nos. 5,290,892, 5,433,746 and 5,403,901, the entire contents of which are incorporated herein by reference although cap 14 should be rigid enough to not collapse when vacuum is applied to the interior of cap 14. Although the soft nature of the material reduces the possibility of snagging or tearing the capsule, cap 14 may be polished, for example, by using the method disclosed in U.S. Pat. No. 5,133,159, the entire contents of which is incorporated herein by reference. In addition, polishing of the molds used to make cap 14 will further reduce possible snagging or tearing of the capsule by cap 14.

This description is given for purposes of illustration and explanation. It will be apparent to those skilled in the relevant art that changes and modification may be made to the invention described above without departing from its scope or spirit.

We claim:

1. An aspiration tip, comprising:
   a) a relatively rigid cannula connected on a proximal end to a hub and open on a distal end; and
   b) a relatively soft, straight tubular cap having a port, the cap sized and shaped to seal the open distal end of the cannula.

2. The apparatus of claim 1 wherein the cap comprises silicone rubber.

3. The apparatus of claim 1 wherein the cannula and hub comprise titanium.

4. The apparatus of claim 1 wherein the cannula and hub comprise stainless steel.

5. The apparatus of claim 1 wherein the cannula and hub comprise plastic.

6. The apparatus of claim 1 wherein the cap comprises a soft acrylic material.

* * * * *